(12) United States Patent
Näfstadius

(10) Patent No.: US 6,969,194 B1
(45) Date of Patent: Nov. 29, 2005

(54) STABLE ROTATABLE RADIATION GANTRY

(75) Inventor: Peder Näfstadius, Täby (SE)

(73) Assignee: PencilBeam Technologies AB, Uppsala (SE)

( * ) Notice: Subject to any disclaimer, the term of this patent is extended or adjusted under 35 U.S.C. 154(b) by 216 days.

(21) Appl. No.: 10/009,262

(22) PCT Filed: May 30, 2000

(86) PCT No.: PCT/SE00/01109

§ 371 (c)(1),
(2), (4) Date: Dec. 10, 2001

(87) PCT Pub. No.: WO00/74779

PCT Pub. Date: Dec. 14, 2000

(30) Foreign Application Priority Data

Jun. 9, 1999 (SE) .................................. 9902163

(51) Int. Cl.7 ............................................... H05G 1/02
(52) U.S. Cl. ........................................ 378/197; 378/65
(58) Field of Search .............................. 378/11, 13, 14, 378/15, 17, 64, 65, 68, 193, 195, 196, 197

(56) References Cited

U.S. PATENT DOCUMENTS

| | | | | |
|---|---|---|---|---|
| 4,115,695 A | * | 9/1978 | Kelman | 378/17 |
| 4,402,085 A | * | 8/1983 | Distler et al. | 378/15 |
| 4,651,007 A | * | 3/1987 | Perusek et al. | 378/15 |
| 4,741,015 A | * | 4/1988 | Charrier | 378/196 |
| 5,473,657 A | | 12/1995 | McKenna | |
| 5,485,502 A | * | 1/1996 | Hinton et al. | 378/117 |
| 5,661,773 A | * | 8/1997 | Swerdloff et al. | 378/65 |
| 5,717,732 A | * | 2/1998 | Tam | 378/4 |
| 5,717,735 A | * | 2/1998 | Ramsdell et al. | 378/208 |
| 5,751,781 A | | 5/1998 | Brown et al. | |
| 5,760,402 A | * | 6/1998 | Hug et al. | 250/363.05 |
| 5,778,047 A | * | 7/1998 | Mansfield et al. | 378/209 |
| 6,490,477 B1 | * | 12/2002 | Zylka et al. | 600/429 |

OTHER PUBLICATIONS

Townsend et al., The SMART scanner: a combined PET/CT tomograph for clinical oncology, Nov. 1998, 1998 IEEE Nuclear Science Symposium and Medical Imaging Conference, pps 1170-1174.*

* cited by examiner

Primary Examiner—Edward J. Glick
Assistant Examiner—Chih-Cheng Glen Kao
(74) Attorney, Agent, or Firm—Young & Thompson

(57) ABSTRACT

An irradiation device provides a free volume around the longitudinal axis of the body (13) around the body to be irradiated. The supporting parts of a gantry (1, 2) are situated substantially radially with respect to the longitudinal axis. The gantry includes an inner gantry part (1) with at least two supporting locations (S) to an outer gantry portion (2). The support locations (S) are situated at each side of a treatment volume (12). A radiation head (8), mechanically attached to the inner gantry part (1) and arranged to direct radiation to the treatment volume (12) is movable around the treatment volume (12). In preferred embodiments, the parts (20, 21, 22, 23) of the gantry are formed as rings, leaving a free space along the rotational axis (9). A body-supporting couch (10) is arranged along the rotational axis extending through the hollow parts (20, 21, 22, 23). The radiation head (8) is preferably movable in a path also perpendicular to the rotation axis (9).

16 Claims, 10 Drawing Sheets

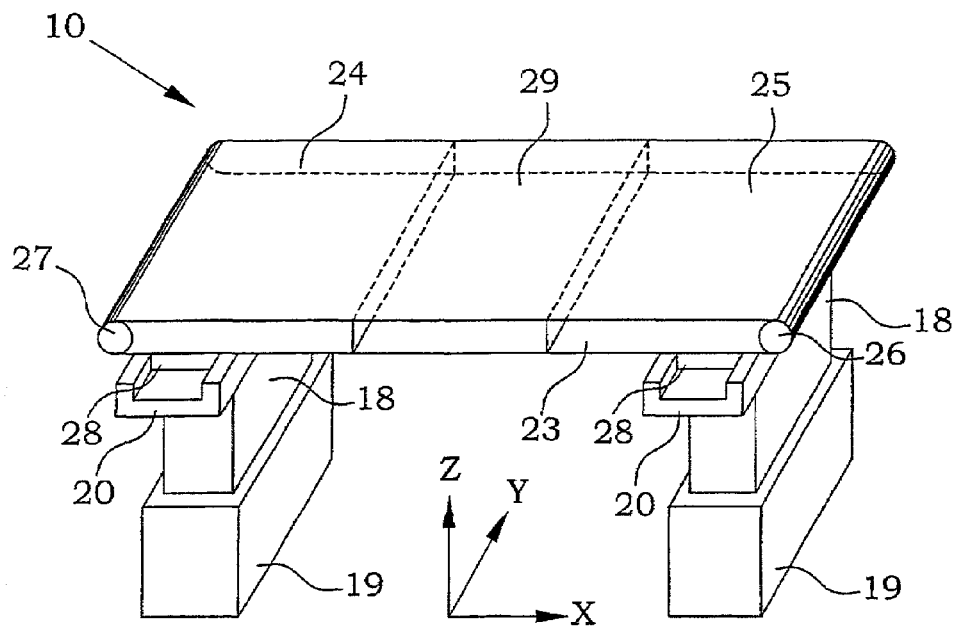
Fig. 3a
Fig. 3b
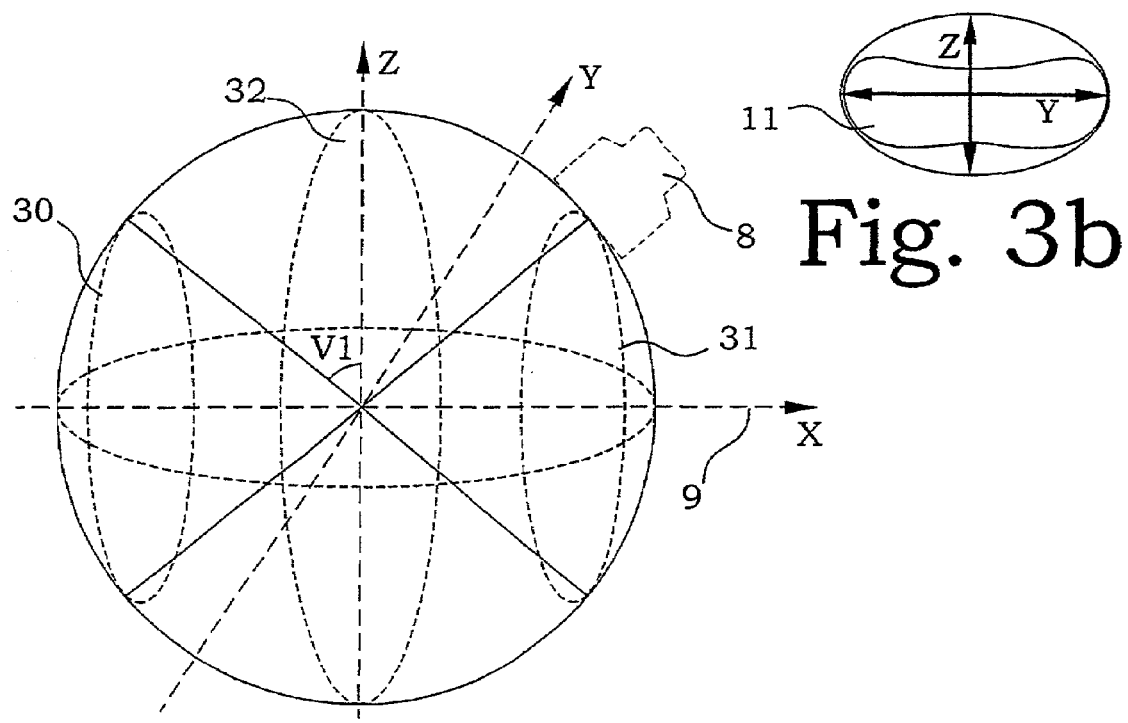
Fig. 4

STABLE ROTATABLE RADIATION GANTRY

TECHNICAL FIELD

The present invention relates to devices and methods for irradiation and in particular to devices and methods for irradiation in more than one direction.

BACKGROUND

Radiation, in the form of electromagnetic radiation or particle radiation, is today used for many purposes, e.g. modification of properties of materials, sterilising purposes as well as medical diagnostics and treatment. The different purposes put different requirements on the methods and devices used, but there are also big similarities.

In the field of radiotherapy and radiosurgery treatment, a common general method is to arrange a patient on a couch. A radiation head is directed relative the patient in order to direct radiation to a certain treatment volume, e.g. a tumour. The general requirement in such applications is to maximise the dose within the treatment volume, while minimise the dose in tissue material outside the treatment volume. One way to accomplish this is to irradiate the treatment volume from different directions, whereby the treatment volume receives a radiation dose at all instances, while certain parts of the surrounding material only receives doses at some occasion.

There are different ways to accomplish multi-directional radiation. For small radiation sources, a multitude of sources may be used. This may e.g. be used for Co-60 sources, which normally are limited in size and weight. For other radiation sources, which are heavier and/or larger, this solution becomes unpractical. Another approach is instead to arrange the radiation head in a movable fashion, e.g. attached to a gantry, which is allowed to move. Since radiation heads often are very heavy, in some cases up to several thousand kilograms, the gantries have typically to be build extremely stable. The easiest way to move the gantry is in such cases to use a rotating movement. Since it in most applications is desirable to have the body to be irradiated positioned horizontally, the rotation axis is typically oriented horizontally, so that the gantry is allowed to move besides and under the body.

The gantry according to prior art is typically designed in a general L or C shape, and the rotational support is provided at one axial end of the body. However, the heavy weights may cause the gantry arms to elastically deform, which results in a modified rotational motion. Instead of a pure rotation, the gantry will precess, creating an inaccuracy in the positioning of the radiation head. Furthermore, the heavy loads will apply extreme forces on the rotation bearings, even if many attempts of balancing the gantries have been made. Due to these reasons, the gantry movements are limited in speed, since high accelerations and retardations increase the load even further.

The couches used together with this type of gantries is typically designed with a support portion, which is situated outside the area of the gantry movement, and a couch sticking into the gantry region substantially horizontally. The reason for this is that no couch supports can be placed in the path of the gantry rotation. Due to the asymmetric design, the couches are typically very sensitive for the positioning of the body on the couch. Placing a body on the couch will typically cause a displacement of up to 1 cm, and changing the location of the body on the couch may alter the displacement several millimeters. This implies that the motion of the couch can not be used during an accurate treatment of e.g. a tumour in the treatment volume.

Since the radiation treatment is intended to be performed also from below, it is important that the couch close to the treatment volume do not absorb the radiation and causes any production of secondary radiation. One way to solve this is to remove most of the solid material from the couch close to the treatment volume, and only leave e.g. a thin stretched foil of material with low cross section for the used radiation. However, in order to support body weight on both sides of the treatment volume, some stiff solid constructions, connecting solid parts of the couch, have to pass relatively close to the treatment volume, e.g. in the form of C-arms or beams. However, changing the irradiation direction, may lead to collisions with such arms, which has to be movable, depending on the position of the radiation head.

Using gantries with a single rotational movement allows for irradiation in different directions in one and the same plane, so called coplanar irradiation. If the ratio between the doses of the treatment volume and the tissues outside, respectively, is going to be increased further, radiation in directions outside this irradiation plane has to be accomplished, so called non-coplanar irradiation. A trivial solution could be to provide the gantry with several radiation heads, irradiating the treatment volume in different out-of-plane directions. However, expensive or heavy radiation heads are not suitable for such solutions.

There are several attempts for solutions giving non-coplanar irradiation in prior art. Some uses radiation deviation means, or uses the possibility to tilt the body to be irradiated. Deviation means are, however, often difficult to control in an exact way, in particular when constant radiation beam properties are concerned. Tilting of the body is unsuitable due to risks of displacements, between the body and the couch, of the couch itself as well as displacements within the body.

The British patent GB 1,129,653 discloses a device for radiation therapy, which is movable in several directions. It discloses the possibility to rotate a gantry around a horizontal axis and at the same time displace the radiation head along a perpendicular circular arch relative to the gantry. This solution provides non-coplanar irradiation, but still performs the problems with instability in the gantry and couch.

The American patent U.S. Pat. No. 5,577,094 discloses another solution, where the gantry is movable along two perpendicular circular paths. This is, besides the earlier described stability problems also restricted mainly to cranial treatments, since the available space around the treatment volume substantially is restricted to one side.

A common problem with most equipment according to the state of the art is that there is a risk for collision between the radiation head and the body, to be irradiated, or couch. When changing irradiation directions, a manual inspection is normally required during movements of the radiation head and/or gantry to ensure that the body is not jammed between the couch and the gantry. This problem makes any requested automation of the treatment difficult. There are some solutions of this problem, which are based on contact switches, which stops any movement, if any distances become too small. Normally, this is combined with using friction safety clutches, applied to the gantry movement. When using such solutions, the maximum allowed moment on the gantry is reduced, which further reduces the maximum retardation and acceleration. Furthermore, the contact switch solution has some reaction time, which put restrictions on the maximum speed of any motion.

The international patent application WO 89/08269 discloses an X-ray tomography apparatus. The apparatus is mounted for rotation around a patient within a circular frame. The apparatus can be displaced along the patient irradiating parallel sections of the body. However, facilities for non-coplanar irradiation are neither discussed nor easily provided for in this apparatus.

SUMMARY

It is therefore a general object of the present invention to provide irradiation devices, which do not present the problems discussed above. In more detail, it is an object of the present invention to provide irradiation devices, which presents an improved stability in the gantry and couch. A further object with the present invention is to provide irradiation devices, which can provide accurate non-coplanar irradiation without involving movement of the body to be irradiated. Another object of the present invention is to provide a design of irradiation devices, which simplifies automatic control of the movements of different parts, without risk for collisions. Yet another object of the present invention is to provide irradiation devices which can provide radiation continuously over an angle considerably exceeding a full turn.

The above objects are achieved by a device and a method according to the enclosed claims. In general, the objects of the present invention are achieved by providing an irradiation device providing a free volume around the body to be irradiated, along its entire longitudinal axis. The supporting parts of a gantry of the irradiation device are situated substantially radially with respect to the free volume. The gantry comprises an inner gantry part with at least two supporting locations to an outer gantry part. The support locations are situated at each side of a treatment volume. A radiation head, mechanically attached to the gantry and arranged to direct radiation to the treatment volume is movable around the treatment volume. In preferred embodiments, parts of the inner and outer gantry parts are formed as rings, leaving a free space along the longitudinal axis of the body. A body-supporting couch is arranged along the rotational axis and through the hollow gantry parts. The radiation head is preferably movable along a path also perpendicular to the rotation axis. Non-coplanar treatments are thereby possible to obtain. The arrangements are suitable for applying numerical control of the gantry movements.

BRIEF DESCRIPTION OF THE DRAWINGS

The invention, together with further objects and advantages thereof, may best be understood by referring to the following description taken together with the accompanying drawings, in which:

FIG. 3a is a perspective view of a couch to be used with an irradiation device according to the present invention;

FIG. 3b illustrates the movement region required for the couch;

FIG. 4 is a schematic drawing illustrating the irradiation directions achievable by a device according to the first embodiment of the present invention;

DETAILED DESCRIPTION

Figure 1:
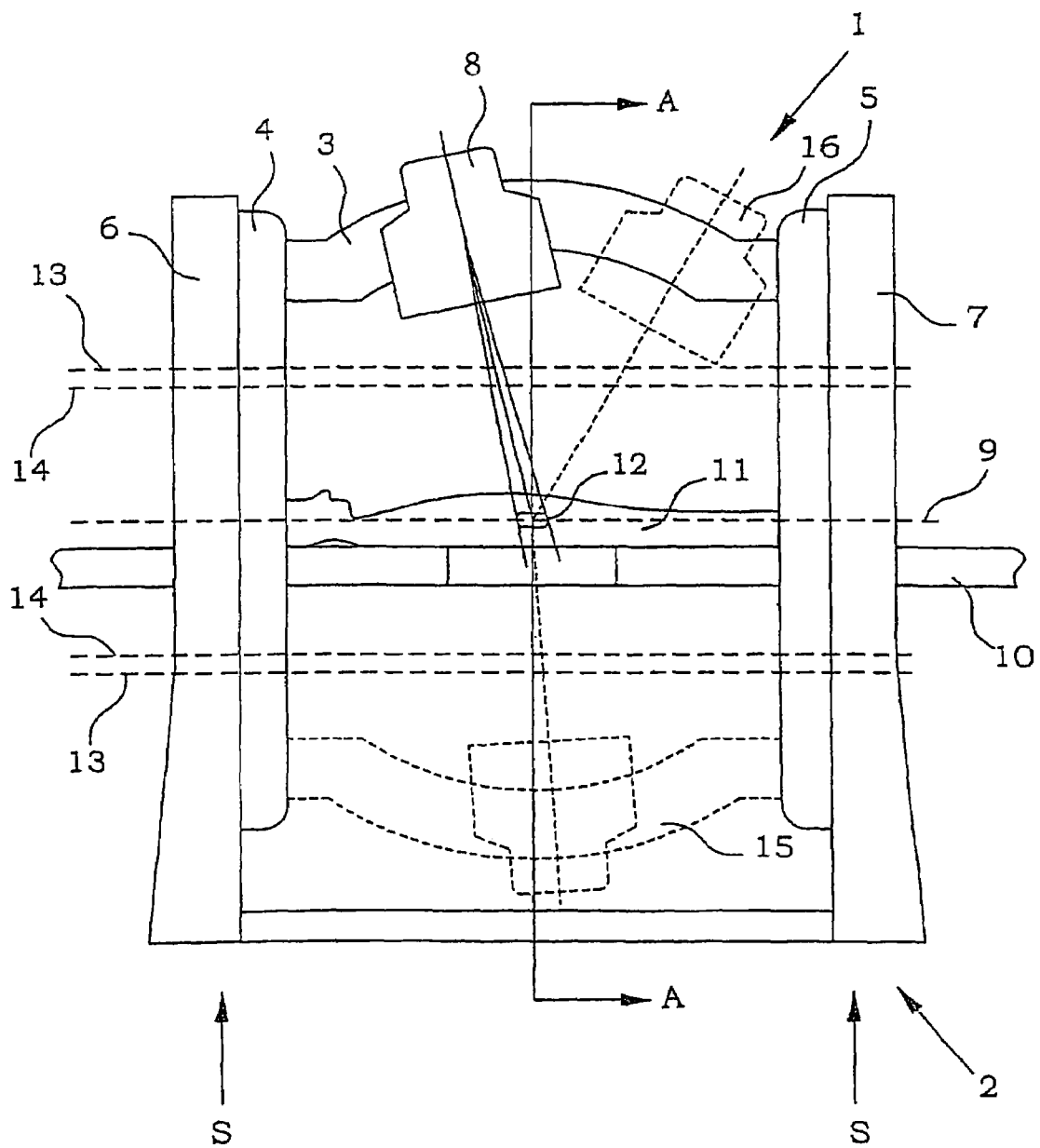
FIG. 1 is a side view of a first embodiment of an irradiation device according to the present invention.

The present invention is based on some general more or less pure geometrical considerations. The stability problems for gantries and couches according to the state of the art are based on the alignment of the gantry support and the couch. The gantry is normally placed substantially in the vicinity of the axis of rotation, which is substantially aligned with the extension of the couch. The couch is only possible to support in one end due to the interference with the gantry movements and the unstable gantry design is based on requirements not to disturb the couch more than necessary.

In the present invention, the geometric considerations are changed. In order to make it possible to provide a stable couch design, a volume around the couch, comprising the volume in which the body to be irradiated is placed, is reserved for couch parts only. No gantry parts are allowed to be present within this volume. All movable parts of the gantry are in all possible situations situated at a distance from the rotation axis of the radiation head which is larger than a predetermined value. The free volume is extended along the couch axis through the entire gantry arrangement. The gantry is supposed to be movable around this reserved volume, irradiating the body from different directions.

As a result of this volume reservation, the gantry is no longer allowed to be placed axially with respect to the couch, the body and the rotation axis. The gantry supporting parts thus have to be moved from an axial position to a radial position, with respect of the couch. That means that the supporting means of the gantry has to be placed substantially above, below or at the sides of the couch.

The gantry design has to be stable, but at the same time allow for examination of the body to be treated. Since the gantry, in a radial position with respect to the body, occupies the same volumes that are used for e.g. visual or manual examination of the body, the gantry thus has to be kept relatively small in size. This complicates the stability problems even more. According to the present invention, the stability of the gantry is achieved by arranging an inner gantry part with two supporting locations relative to an outer gantry part. These two supporting locations are placed at each side of the treatment volume, i.e. the volume of the body that is to be irradiated. Since there are two support locations, the stability of the gantry is increased, without increasing the volume or inherent strength of the gantry. The two support locations may be placed in any direction, radially or axially, as long as the free volume around the couch is preserved.

Below, four embodiments of the present invention are described, which illustrates devices where the supporting locations of the inner gantry part to the outer gantry part are placed in different directions relative to the treatment volume. The invention is particularly useful for radiotherapy and radiosurgery applications. However, as anyone skilled in the art understands, there are other modifications and alternative embodiments, which still are covered by the scope of the invention.

In FIG. 1, a side view of a first embodiment of an irradiation device according to the invention is illustrated. A radiation head 8 is mechanically supported by an inner gantry part, generally denoted by 1. The inner gantry part 1 comprises in the present embodiment a circle arc portion 3, a first ring portion 4 and a second ring portion 5. The radiation head 8 is movable along the circle arc portion 3, and arranged to direct radiation to a treatment volume 12. A body 11 is placed at a body-supporting couch, generally denoted by 10. The treatment volume 12 is thereby in the normal case a part of the body 11, which is going to be treated by the radiation emitted from the radiation head 8. The first ring portion 4 and a second ring portion 5 are in this embodiment positioned at each side of the treatment volume 12. The ring portions 4, 5 are rotatably supported by an outer gantry part 2, comprising a first support portion 6 and a second support portion 7. Accordingly, the inner gantry part 1 is provided with two supporting locations S with respect to the outer gantry part 2. The inner gantry part 1 is by this arrangement possible to rotate around a rotation axis 9, which is substantially horizontal. In the present invention, the two supporting locations S are situated on each side of the treatment volume 12, in an axial direction, i.e. in the direction of the rotation axis 9. The treatment volume 12 is in a preferred embodiment positioned at the rotation axis 9.

The inner gantry part 1 is rotatable around the rotation axis 9, and may thus be used also to irradiate the treatment volume 12 from below, as indicated by the broken line structure 15. The radiation head 8 is movable along the circle arc portion 3 and the broken line head 16 illustrates one end position for the radiation head 8. The motion of the inner gantry part 1 and the radiation head 8 between the supporting locations S of the inner gantry part 1 always takes place outside a cylindrical volume, which is indicated by the broken line 13. No movable parts of the inner gantry part 1 will ever exist within this gantry rotational envelope 13, independent of the intended motion of the radiation head 8. The gantry rotational envelope 13 thus constitutes the free volume around the body to be treated 11. The body to be treated 11 and the couch 10 are both preferably enclosed within a second cylindrical volume, a body positioning volume 14. This body positioning volume 14 is totally enclosed by the gantry rotational envelope 13, preferably with a certain security margin. In such a case, there is no risk for jamming of the body 11 against the couch 10 or destruction of the radiation head 8 against the couch 10 at any time. This implies that the couch 10 can not have any supporting portions against e.g. floor or ceiling in the space between the supporting locations S of the inner gantry part 1.

Figure 2:
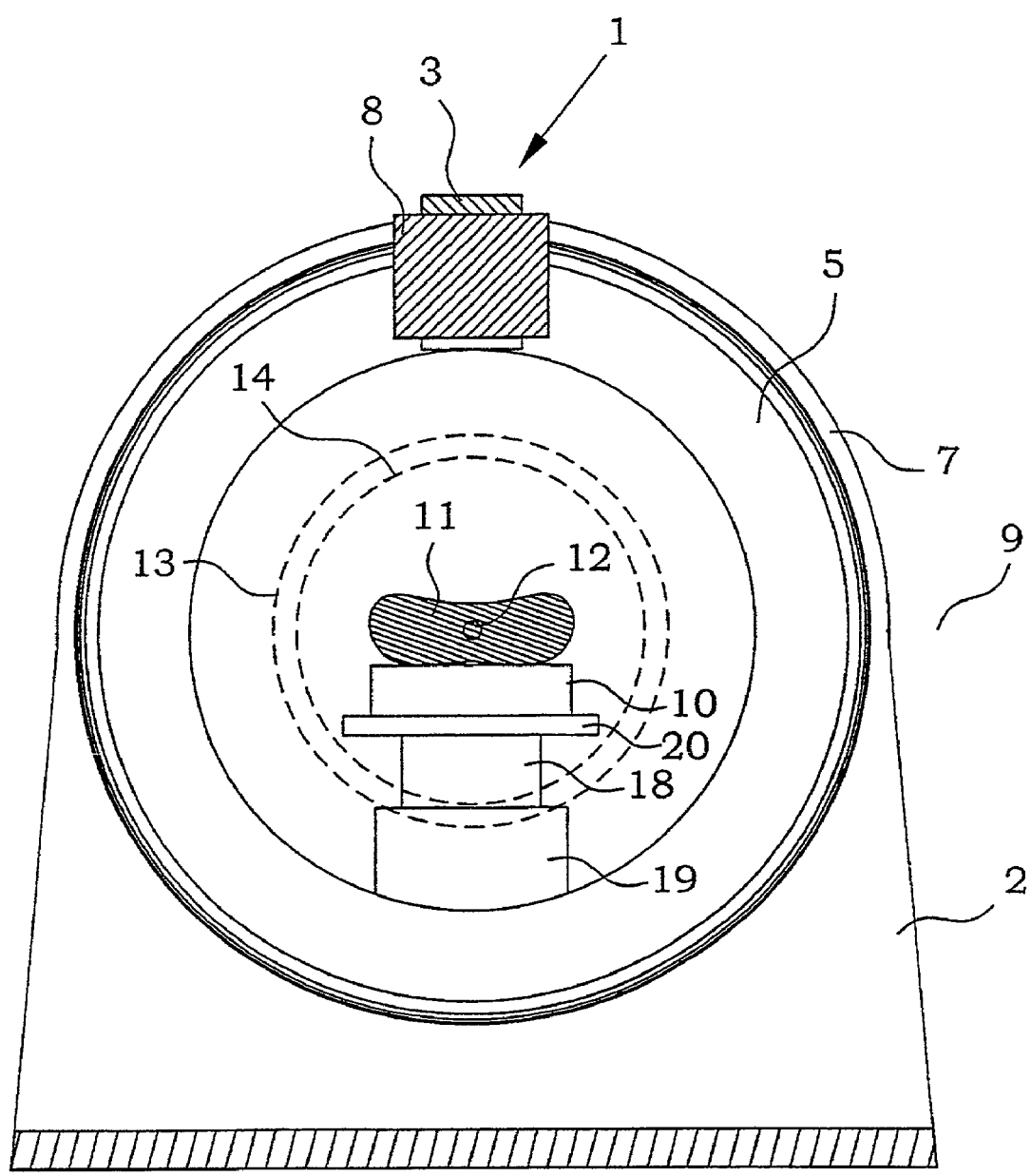
FIG. 2 is a sectional view of the irradiation device of FIG. 1, taken along the line A—A.

A preferable solution of the couch-supporting problem is illustrated in FIG. 2, where the irradiation device of FIG. 1 is illustrated in a sectional view along the line A—A in the axial direction. The ring portions 4, 5 of the inner gantry part 1 are designed with a substantially circular shape, defining rotationally symmetric outer surfaces. These rotationally symmetric outer surfaces form the bearing locations of the inner gantry part 1. The support portions 6, 7 are in a corresponding manner designed with rotationally symmetric inner surfaces. The support portions 6, 7 are adapted to fit the ring portions 4, 5, leaving appropriate space for bearings, in the form of e.g. roller bearings. Since the ring portions 4, 5 and the support portions 6, 7 are formed without any parts along the rotation axis 9, there is free space available. The couch may thus extend through the ring portions 4, 5 and the support portions 6, 7, along the rotation axis 9. The couch 10 may therefore be supported by the outer gantry part 2 or, as shown in the figure, by separate supports outside the inner gantry part bearing locations. In this embodiment, the couch support is movable in height and horizontally, perpendicular to the rotation axis 9. This two-dimensional mobility is accomplished by means in the couch supports. In FIG. 2, a slot portion 20 allowing for horizontal movement, and a piston 18 and cylinder 19 for vertical movement are shown. The couch 10 and its supports are described more in detail below.

FIG. 3a illustrates a perspective view of a preferred embodiment of a couch 10 according to the present invention. The couch comprises a first couch support portion 21 and a second couch support portion 22. As discussed above, the couch support portions 21, 22 may be integrated in the gantry support or provided as separate means. From the first couch support section 21, a first rigid couch portion 23 extends towards the treatment volume. From the second couch support portion 22, a second rigid couch section 24 extends towards the treatment volume, in the opposite direction. The front parts of the rigid couch sections 23, 24 are placed apart from each other and thereby form an empty volume 29 there between. This empty volume 29, at operation of the irradiation device, is situated just beneath the treatment volume 12 (see FIG. 1). The rigid sections 23, 24 are preferably interconnected by a thin foil 25 of material with a low radiation cross section, e.g. polyethylene. The foil 25 is in this embodiment provided as an endless belt, which is driven by two rolls, 26, 27, and may thus serve for changing the position of the body along the rotation axis. Alternatively, rigid plates of e.g. carbon fibre may be used instead of the thin foil.

The rigid sections 23, 24 are in a preferred embodiment movable relative the gantry. Preferably, the displacements are possible in at least two translation directions, vertically, and horizontally and perpendicular to the rotation axis 9, respectively. According to FIG. 3a, these directions are denoted z and y, respectively. The y-motion of the rigid sections 23, 24 is in the present embodiment accomplished by letting a protrusion 28 of the rigid sections 23, 24 slide in a slot portion 20. Any conventional means for causing and controlling this motion may be used. The z-motion of the rigid sections 23, 24 is in the present embodiment accomplished by a piston 18 of the couch support portions 21, 22 which can be moved up and down in a cylinder 19. In a preferred embodiment, the motion of the rigid sections 23, 24 are independent of each other, which provides for various positioning possibilities for the body. As indicated above, the foil 25 may be used for changing the position of a body on the couch 10 in the x-direction, by driving the endless belt by the two rolls 26 and 27.

FIG. 3b illustrates a cross section of a body to be irradiated. The motion possibilities of the couch should be such that all parts of the body would be possible to position at the treatment volume. The limit movements in the z and y directions should therefore enclose the body volume, or at least the parts of the body volume, which may be a target for irradiation.

Now referring again to FIG. 1 and FIG. 2, the cooperation between the couch and the gantry is easily understood. The inner gantry part 1 is rotatably supported by the outer gantry part 2. The couch 10 extends from both ends along the rotation axis 9, leaving the open space 29 beneath the treatment volume 12. The couch support portions 21, 22 are provided outside the inner gantry part support locations S. When the inner gantry part 1 is rotated around the couch 10, the treatment volume 12 is available from all directions without any radiation disturbing material, except for the thin stretched foil 25.

It is easily seen in FIGS. 1 and 2, that the gantry is supported mainly in the radial direction, with respect of the rotation axis 9. The circular design of the ring portions 4, 5 and the support portions 6, 7 enables the clearance of the volume around the couch 10. It is also seen that since the centre of mass of the inner gantry part 1 always is situated between the support locations S, there are relatively low bending moment present in the gantry.

In a preferred embodiment, the inner gantry part 1 is continuously rotatable; relative the outer gantry part 2. The mechanical operation and support is easily provided with e.g. conventional gear solutions and bearings. One limiting factor in equipment existing today is the wiring for the radiation head. However, by introducing sliding contacts between the inner gantry part 1 and the outer gantry part 2, preferably in connection with the mechanical bearing, a true continuous rotational motion may be achieved.

Returning to FIG. 1, the radiation head 8 is movable along a circle arc portion 3 of the inner gantry part 1. The circle arc portion 3 has a centre of curvature, which is situated within the treatment volume 12, and preferably on the rotation axis 9. When the radiation head 8 is moved along the circle arc portion 3, it maintains the radiation direction towards the treatment volume 12. By combining the rotation around the horizontal axis 9 and the motion along the circle arc portion 3, a multitude of irradiation directions may be reached. During such movements, the radiation head 8 is situated at the same distance from the treatment volume 12.

The treatment situation is schematically illustrated in FIG. 4. The radiation head 8 is possible to move anywhere along a spherical surface, which is cut by two parallel vertical planes 30, 31, perpendicular to the rotation axis 9. All directions within an angle V1 from a centre vertical plane 32 are achievable. A non-coplanar treatment may be achieved. Other angles than perpendicular to the rotation axis may be of interest to use in order to avoid damage of vital organs situated in the vicinity of the treatment volume 12. If the radiation head 8 is fixed at a certain position along the circle arc portion 3 and the inner gantry portion 1 is rotated, the irradiation of the treatment volume 12 will be applied in a conical shape. If the displacement the radiation head 8 is controlled simultaneously as the inner gantry part 1 moves, any other geometrical irradiation pattern may be accomplished. In this way an irradiation path on the treatment volume may be adapted to each individual case, depending on the nature of the target and the sensitivity for radiation damage in the surroundings of the treatment volume 12.

The possibility of continuous rotation together with the possibility to change the angle of the radiation head perpendicular to the rotation axis facilitates different treatment possibilities. If several non-coplanar irradiation paths are to be performed, the paths may be scheduled without taking any limitations in the rotation into account. The path may e.g. be selected as a continuous spherical shaped coil around the treatment volume 12.

The above treatments are preferably performed in an automated manner. Since the irradiation devices according to the present invention almost totally removes the risks for mechanical jamming or contact destruction, the operational processes may be automated easily. The possibility to spread the radiation dose over a larger volume around the treatment volume is used more efficiently, if short exposures from a multitude of directions are given. This requires a rapid movement of the radiation head, which is facilitated by the stable gantry construction according to the present invention. Furthermore, since the gantry construction according to the present invention reduces the risk for jamming considerably, other approaches of control may be implemented.

The motion of the radiation head in the two perpendicular directions may preferably be performed utilising numerical control procedures. In such a system, the coordinates of the radiation head may easily be controlled together with e.g. radiation intensity, radiation distribution etc. in order to tailoring a radiation treatment. Revolution times of the inner gantry part of the order of 5 s would be possible, enabling the radiation head to move between two arbitrary selected positions in times of the same order of magnitude.

The motion of the couch may also be controlled automatically. However, there is a general request not to move the body during treatment, so the main purposes for automatic control of the couch movement is to facilitate the introduction of the body into the area of the treatment volume.

Figure 5:
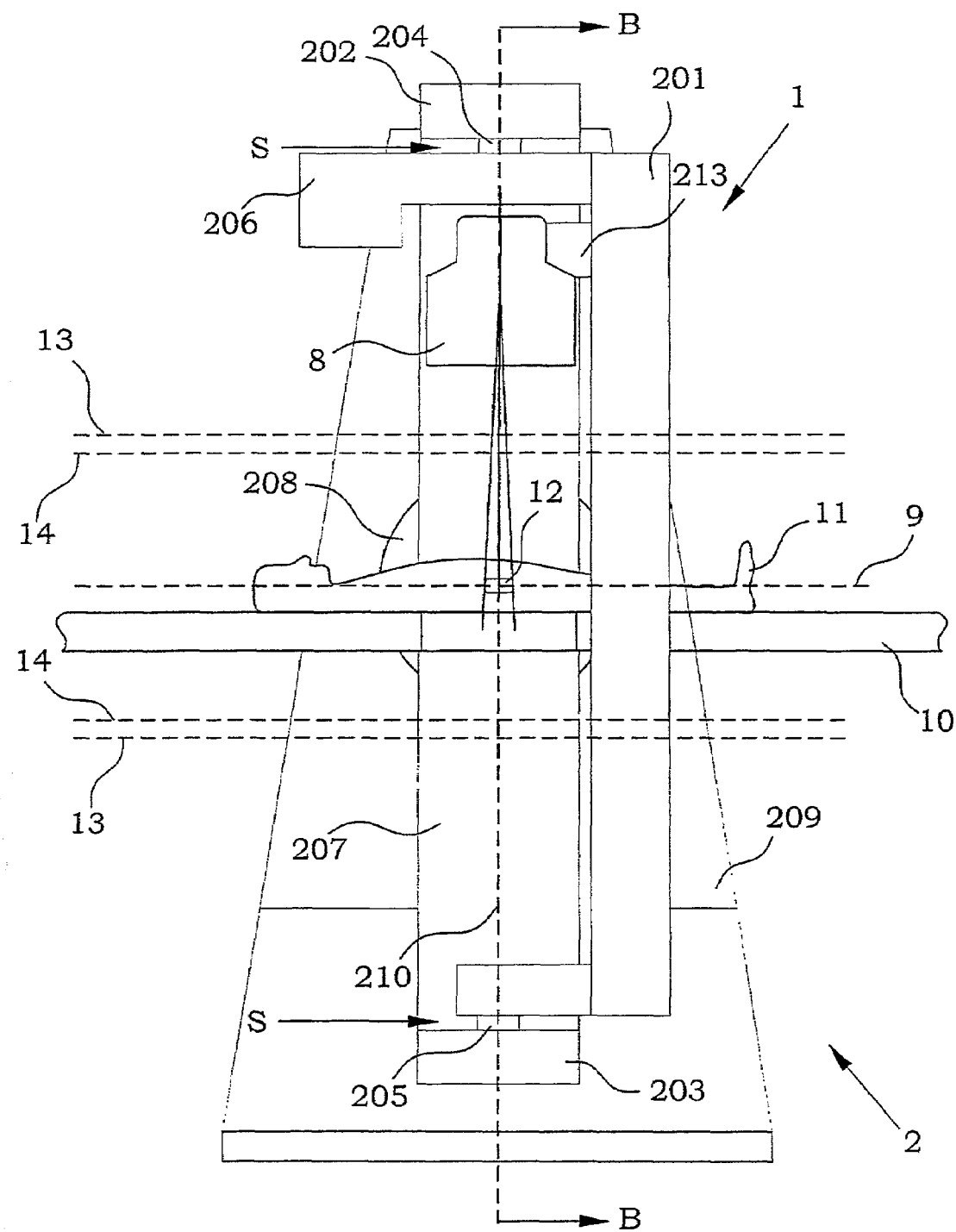
FIG. 5 is a side view of a second embodiment of an irradiation device according to the present invention.
Figure 6:
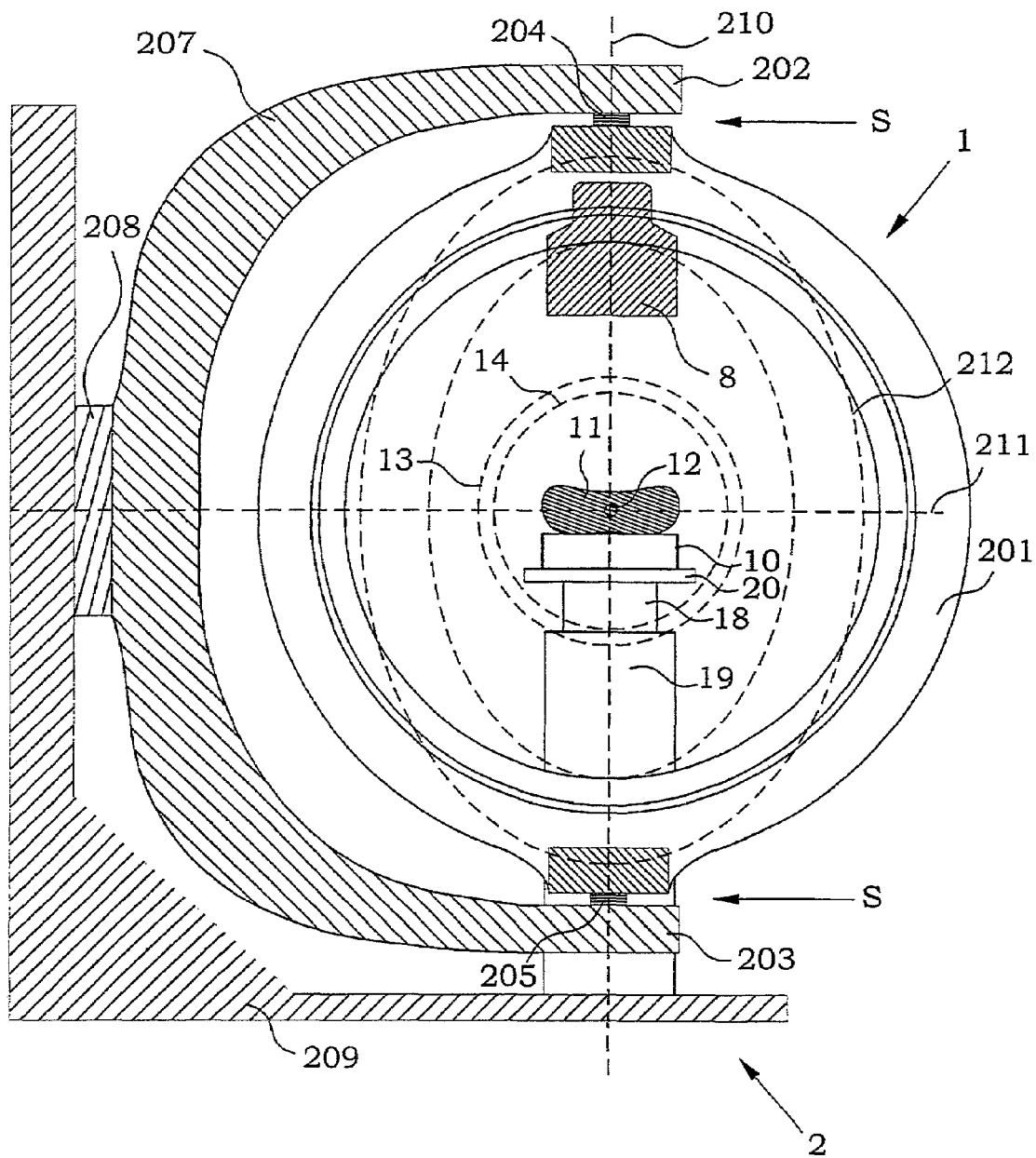
FIG. 6 is a sectional view of the irradiation device of FIG. 7, taken along the line B—B.

In FIG. 5, a side view of a second embodiment of an irradiation device according to the invention is illustrated. In FIG. 6 the irradiation device of FIG. 5 is illustrated in a sectional view along the line B—B in the axial direction. A radiation head-8 is mechanically supported by an inner gantry part, generally denoted by 1. The inner gantry part 1 comprises in the present embodiment a head supporting arm 213, a ring portion 201 and a counterweight 206. The radiation head 8 is fixed at the head supporting arm 213, and arranged to direct radiation to a treatment volume 12. A body 11 is placed at a body-supporting couch, generally denoted by 10. The treatment volume 12 is thereby in the normal case a part of the body 11, which is going to be treated by the radiation emitted from the radiation head 8. The head supporting arm 213 is movable along the ring portion 201, which means that the radiation head is able to rotate around a rotation axis 9, which is substantially horizontal. The treatment volume 12 is in a preferred embodiment positioned at the rotation axis 9.

The inner gantry part 1 is supported, via a first rotational support 204 and a second rotational support 205, by an outer gantry part 2. The outer gantry part 2 comprises in this embodiment a generally C-shaped jaw portion 207, and a support portion 209. The jaw portion 207 surrounds the treatment volume 12 and is rotationally attached in its back end to the support portion by a rotational connection 208. The first rotational support 204 and the second rotational support 205 are attached to the front ends 202 and 203, respectively, of the jaw portion 207, and are therefore positioned at each side of the treatment volume 12, in the vertical direction. Accordingly, the inner gantry part 1 is provided with two supporting locations S with respect to the outer gantry part 2. The supporting locations S are situated on each side of the treatment volume 12, in a radial direction.

The radiation head 8 is rotatable around the rotation axis 9, and may thus be used also to irradiate the treatment volume 12 from below. In order to reach non-coplanar irradiation directions, the inner gantry part 1 is rotated, either around a vertical axis 210 by the first and second rotational supports 204, 205, or around a horizontal axis 211 by the rotational connection 208. A slight rotation of the inner gantry part 1 will put the ring portion 201 as indicated by the broken line ring 212. Such a tilting will thus limit the free space around the couch 10 and body 11, and a restriction of this tilting is necessary to ensure a free space around the body. The first and second rotational supports 204, 205 are situated in the same plane as the radiation head 8, while the ring portion 201 is slightly offset, as clearly seen in FIG. 5. The axes of the tilting of the inner gantry part 1, either the vertical axis 210 or the horizontal axis 211, are intersecting the treatment volume 12. This means that the radiation head 8 always is directed substantially towards the treatment volume 12.

The tilting of the inner gantry part 1 and the radiation head 8 is restricted in such a manner that all parts of the gantry and radiation head 8 are located outside a cylindrical volume, which is indicated by the broken line 13. No movable parts of the inner gantry part 1 will ever exist within this gantry rotational envelope 13, independent of the intended motion of the radiation head 8 or tilting of the inner gantry part 1. The gantry rotational envelope 13 thus constitutes the free volume around the body to be treated 11. The body to be treated 11 and the couch 10 are as in previous embodiment both preferably enclosed within a second cylindrical volume, a body positioning volume 14. This body positioning volume 14 is totally enclosed by the gantry rotational envelope 13, preferably with a certain security margin. In such a case, there is no risk for jamming of the body 11 against the couch 10 or destruction of the radiation head 8 against the couch 10 at any time.

The ring portion 201 of the inner gantry part 1 is designed with a substantially circular shape. This means that the ring portion 201 is formed without any parts along the rotation axis 9, where free space is available. The couch 10 may thus extend through the ring portion 201, substantially along the rotation axis 9. When the ring portion 201 is tilted in any direction, the rotation axis 9 of the radiation head 8 is also tilted. However, since the tilting is restricted to relatively small angles, the angular deviation between the longitudinal axis of the couch and body, and the rotation axis, is also relatively small.

In FIG. 5, it may be noticed, that since the first and second rotational supports 204, 205 are situated in the same plane as the radiation head 8 and the ring portion 201 is displaced from the axis 210, the ring portion 201 applies a torque on the outer gantry part 2, which would tend to rotate the rotational connection 208. In order to compensate for this torque, a counterweight 206, is attached to the ring portion 201. The counterweight 206 balances the weight of the ring portion 201. The counterweight 206 is fixed to the ring portion 201 and do not follow the rotation of the radiation head 8. This makes it possible to locate the counterweight in an area, which is not required for access to the body.

Figure 7:
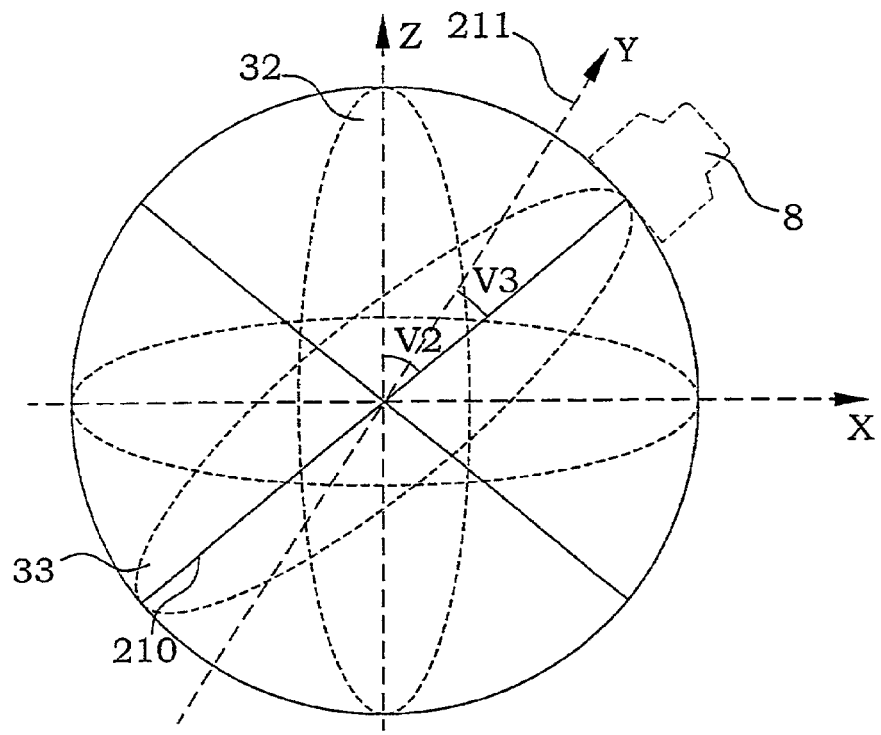
FIG. 7 is a schematic drawing illustrating the irradiation directions achievable by a device according to the second embodiment of the present invention.

The treatment situation in a device according to the second embodiment of the present invention is schematically illustrated in FIG. 7. The radiation head 8 is possible to move anywhere along a spherical surface, which is restricted by an angle V2 from the vertical axis and an angle V3 from the axis 211. All directions within these angles are achievable. A non-coplanar treatment may thus be achieved. Other angles than perpendicular to the rotation axis may be of interest to use in order to avoid damage of vital organs situated in the vicinity of the treatment volume 12. If the inner gantry part 1 is fixed at a certain position with respect to the outer gantry part 2, the rotational connection 208 is at a fixed angle and the radiation head 8 is rotated, the irradiation of the treatment volume 12 will be applied in a plane 33 defined by the axis 210. If the tilting of the gantry is controlled simultaneously as the radiation head 8 rotates, any other geometrical irradiation pattern may be accomplished. In this way an irradiation path on the treatment volume 12 may be adapted to each individual case, depending on the nature of the target and the sensitivity for radiation damage in the surroundings of the treatment volume 12.

It is easily seen in FIGS. 5 and 6, that the gantry is supported mainly in the radial direction, with respect of the longitudinal axis of the couch, and the rotation axis 9. The circular design of the ring portion 201 enables the clearance of the volume around the couch 10.

Figure 8:
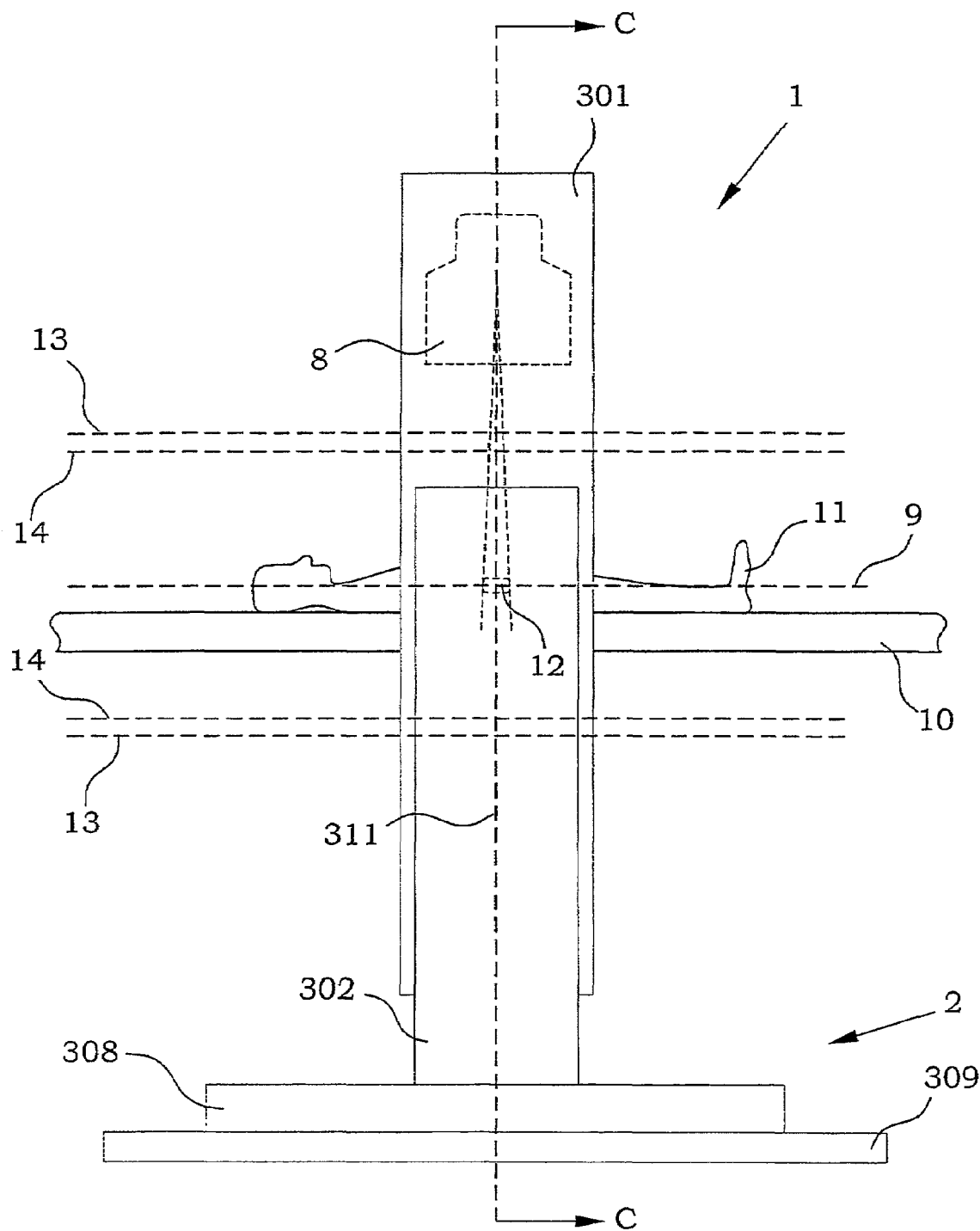
FIG. 8 is a side view of a third embodiment of an irradiation device according to the present invention.
Figure 9:
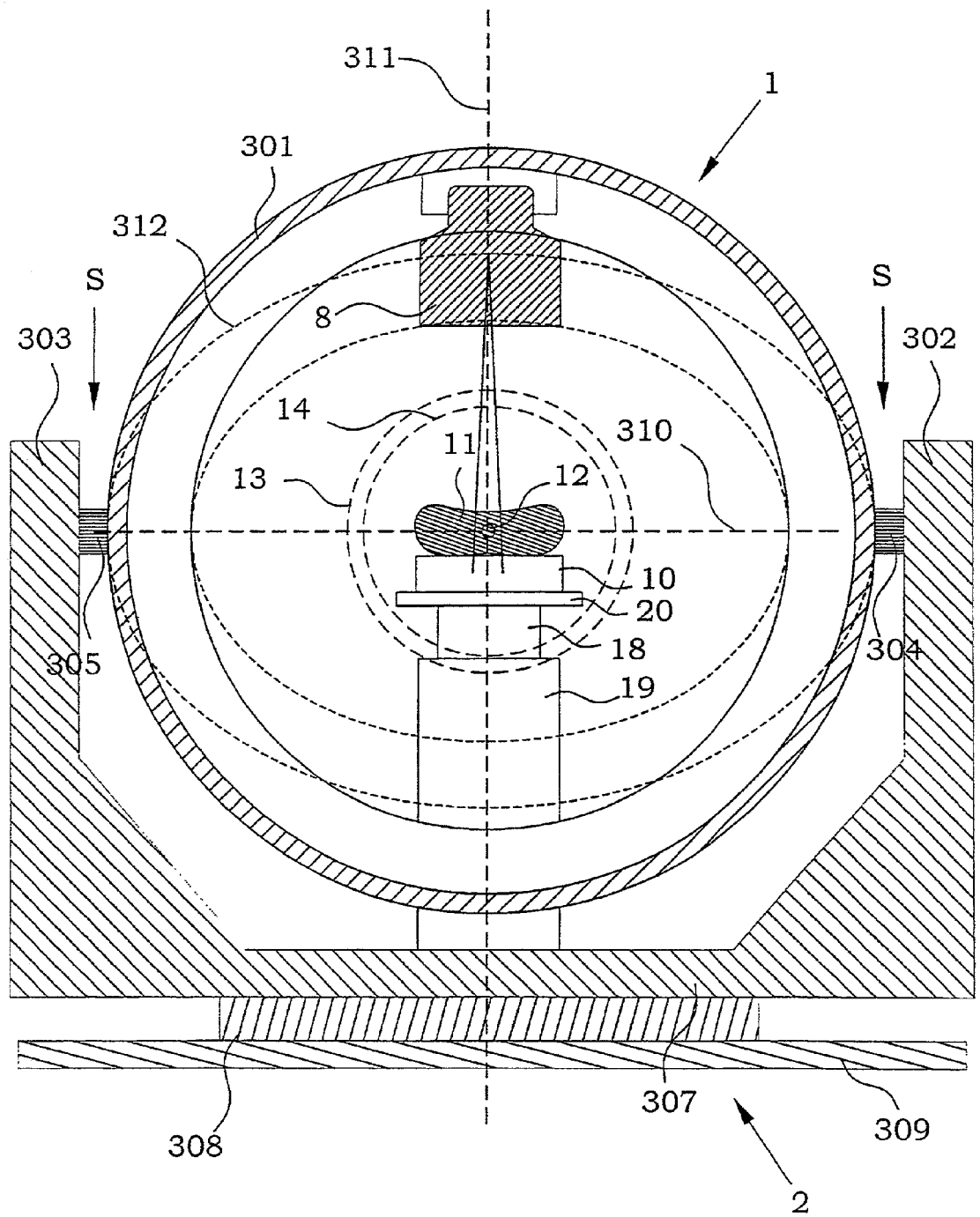
FIG. 9 is a sectional view of the irradiation device of FIG. 8, taken along the line C—C.

In FIG. 8, a side view of a third embodiment of an irradiation device according to the invention is illustrated. In FIG. 9 the irradiation device of FIG. 8 is illustrated in a sectional view along the line C—C in the axial direction. A radiation head 8 is mechanically supported by an inner gantry part, generally denoted by 1. The inner gantry part 1 comprises in the present embodiment a ring portion 301. The radiation head 8 is arranged to direct radiation to a treatment volume 12. A body 11 is placed at a body-supporting couch, generally denoted by 10. The treatment volume 12 is thereby in the normal case a part of the body 11, which is going to be treated by the radiation emitted from the radiation head 8. The radiation head 8 is movable along the ring portion 301, which means that the radiation head 8 is able to rotate around a rotation axis 9, which is substantially horizontal. The treatment volume 12 is in a preferred embodiment positioned at the rotation axis 9.

The inner gantry part 1 is supported, via a first rotational support 304 and a second rotational support 305, by an outer gantry part 2. The outer gantry part 2 comprises in this embodiment a generally U-shaped jaw portion 307, and a support portion 309. The jaw portion 307 surrounds the treatment volume 12 and is rotationally attached in its lower part to the support portion 309 by a rotational connection 308. The first rotational support 304 and the second rotational support 305 are attached to the legs 302 and 303, respectively, of the jaw portion 307, and are therefore positioned at each side of the treatment volume 12, in a horizontal direction, perpendicular to the longitudinal axis of the couch 10 and the body 11. Accordingly, the inner gantry part 1 is provided with two supporting locations S with respect to the outer gantry part 2. The supporting locations S are situated on each side of the treatment volume 12, in a radial direction.

The radiation head 8 is rotatable around the rotation axis 9, and may thus be used also to irradiate the treatment volume 12 from below. In order to reach non-coplanar irradiation directions, the inner gantry part 1 is rotated, either around a horizontal axis 310 by the first and second rotational supports 304, 305, or around a vertical axis 311 by the rotational connection 308. A slight rotation of the inner gantry part 1 will put the ring portion 301 as indicated by the broken line ring 312. Such a tilting will thus limit the free space around the couch 10 and body 11, and a restriction of this tilting is necessary to ensure a free space around the body. The first and second rotational supports 304, 305 are situated in the same plane as the radiation head 8 and the ring portion 301. The axes of the tilting of the inner gantry part 1, either the vertical axis 311 or the horizontal axis 310, are intersecting the treatment volume 12. This means that the radiation head 8 always is directed substantially towards the treatment volume 12.

The tilting of the inner gantry part 1 and the radiation head 8 is restricted in such a manner that all parts of the gantry and radiation head 8 are located outside a cylindrical volume, which is indicated by the broken line 13. No movable parts of the inner gantry part 1 will ever exist within this gantry rotational envelope 13, independent of the intended motion of the radiation head 8 or tilting of the inner gantry part 1. The gantry rotational envelope 13 thus constitutes the free volume around the body to be treated 11. The body to be treated 11 and the couch 10 are as in previous embodiments both preferably enclosed within a second cylindrical volume, a body positioning volume 14. This body positioning volume 14 is totally enclosed by the gantry rotational envelope 13, preferably with a certain security margin. In such a case, there is no risk for jamming of the body 11 against the couch 10 or destruction of the radiation head 8 against the couch 10 at any time.

The ring portion 301 of the inner gantry part 1 is designed with a substantially circular shape. This means that the ring portion 301 is formed without any parts along the rotation axis 9, where free space is available. The couch 10 may thus extend through the ring portion 301, substantially along the rotation axis 9. When the ring portion 301 is tilted in any direction, the rotation axis 9 of the radiation head 8 is also tilted. However, since the tilting is restricted to relatively small angles, the angular deviation between the longitudinal axis of the couch and body, and the rotation axis, is also relatively small.

In FIG. 8, it may be noticed, that the radiation head 8 and the ring portion 301 are situated essentially in the same plane as the treatment volume 12. This means that the access to the treatment volume by visual or mechanical means is restricted. However, the design of the inner gantry part 1 is simplified as compared with the second embodiment, described above. In order to achieve access to the treatment volume, a similar design as in the previous embodiment may be provided, including weight balancing equipment.

Figure 10:
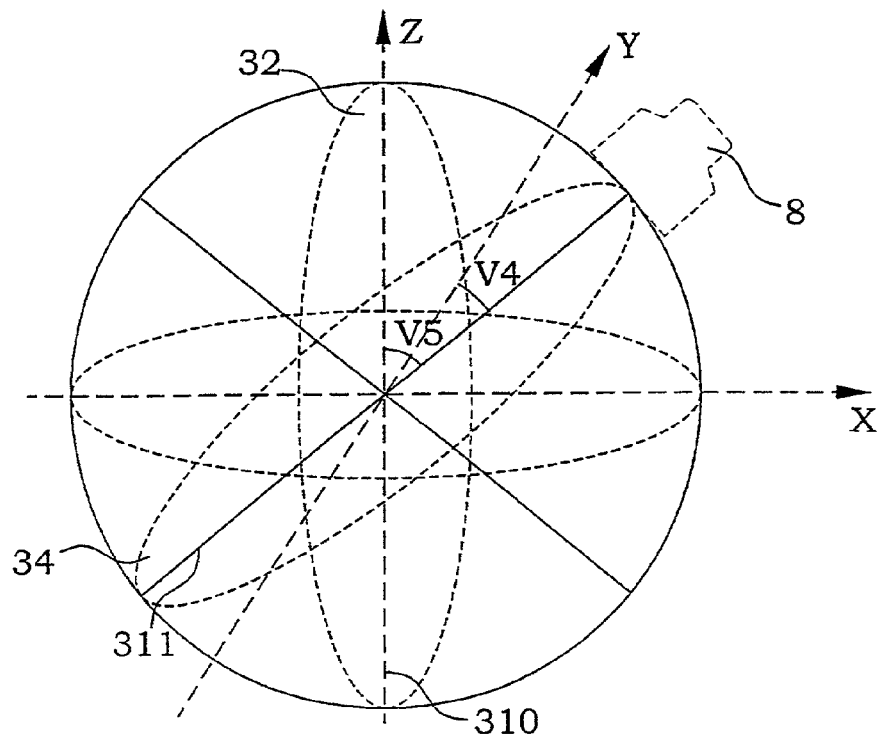
FIG. 10 is a schematic drawing illustrating the irradiation directions achievable by a device according to the third embodiment of the present invention.

The treatment situation in a device according to the second embodiment of the present invention is schematically illustrated in FIG. 10. The radiation head 8 is possible to move anywhere along a spherical surface, which is restricted by an angle V5 from the vertical axis 311 and an angle V5 from a horizontal axis perpendicular to the longitudinal axis of the couch and body. All directions within these angles are achievable. A non-coplanar treatment may thus be achieved. Other angles than perpendicular to the rotation axis may be of interest to use in order to avoid damage of vital organs situated in the vicinity of the treatment volume 12. If the inner gantry part 1 is fixed at a certain position with respect to the outer gantry part 2, the rotational connection 308 is at a fixed angle and the radiation head 8 is rotated, the irradiation of the treatment volume 12 will be applied in a plane 34 defined by the axis 310. If the tilting of the gantry is controlled simultaneously as the radiation head 8 rotates, any other geometrical irradiation pattern may be accomplished. In this way an irradiation path on the treatment volume 12 may be adapted to each individual case, depending on the nature of the target and the sensitivity for radiation damage in the surroundings of the treatment volume 12.

It is easily seen in FIGS. 8 and 9, that the gantry is supported mainly in the radial direction, with respect to the longitudinal axis of the couch, and the rotation axis 9. The circular design of the ring portion 301 enables the clearance of the volume around the couch 10. It is also seen that since the centre of mass of the inner gantry part 1 always is situated between the support locations S, there are relatively low bending moment present in the gantry.

Figure 11:
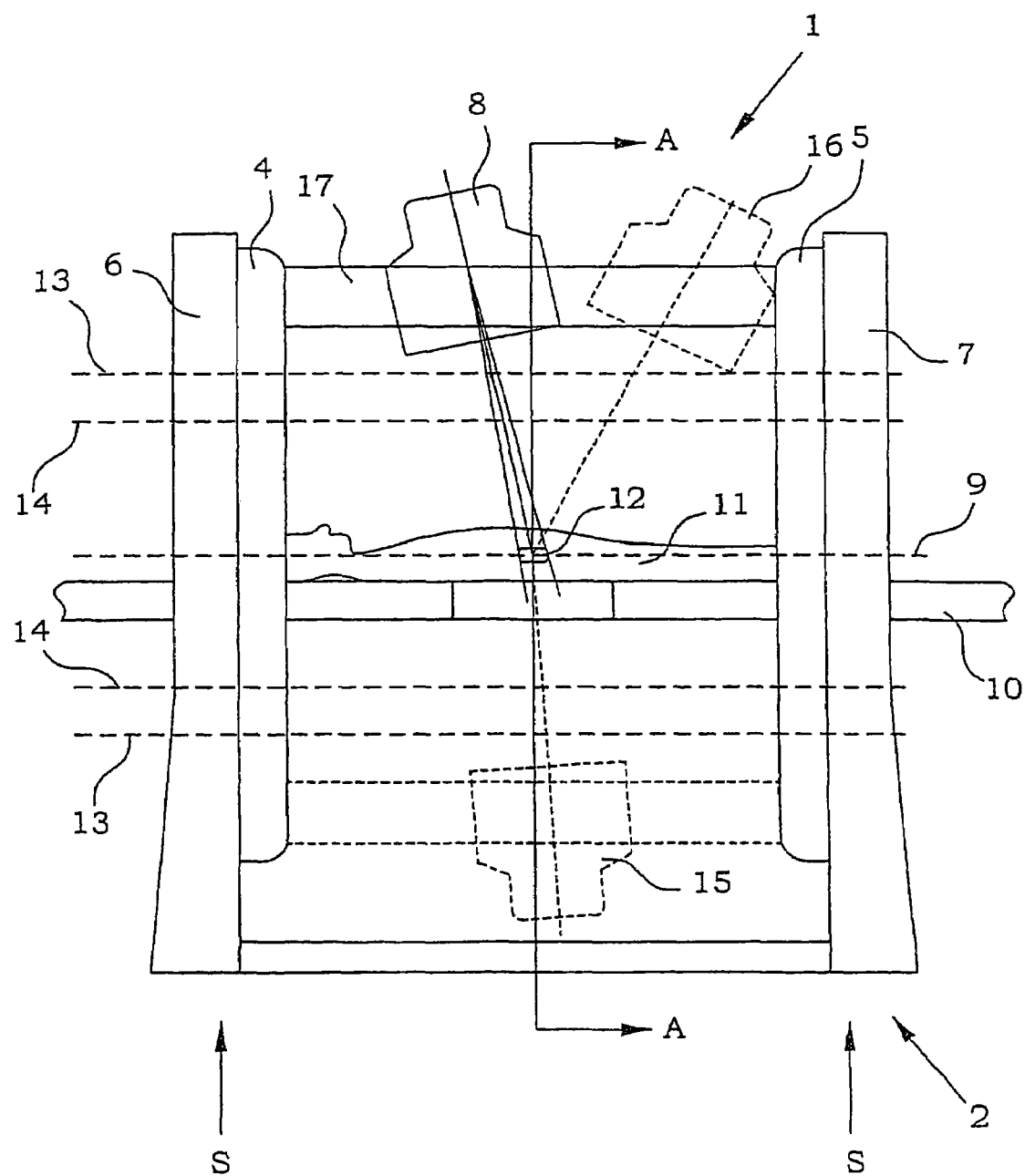
FIG. 11 is a side view of a fourth embodiment of an irradiation device according to the present invention.

In FIG. 11, a fourth embodiment of an irradiation device according to the invention is illustrated. It is very similar to the first embodiment and corresponding parts having the same reference numbers will not be described or discussed again.

This fourth embodiment comprises a linear beam portion 17 interconnecting the first ring portion 4 and the second ring portion 5. The radiation head 8 is movable along the linear beam portion 17. In order to maintain the irradiation directed towards the treatment volume 12, the radiation head 8 is also allowed to be tilted with respect to the linear beam portion 17. This means that the relative angle between the linear beam portion 17 and the radiation head 8 is different in e.g. positions 15 and 16. In order to direct the radiation to the treatment volume 12, the direction of the radiation head 8 has to follow:

$$\alpha = \tan^{-1}\left(\frac{d}{r}\right),$$

where $\alpha$ is the angle from the pure radial direction, d is the displacement of the radiation head 8, and r is the distance from the tilting axis of the radiation head to the rotation axis 9.

Furthermore, the radiation head 8 changes its distance to the treatment volume 12 when it moves along the linear beam portion 17. The distance varies as $$s = \frac{r}{\cos\alpha} = \sqrt{r^2 + d^2},$$

where s is the distance between the tilting axis of the radiation head 8 and the treatment volume. In most applications, it is advantageous if the isocenter distance is constant independent of the irradiation direction. However, one can compensate for the changing isocenter distance in this embodiment, by adapting collimator settings and dose according to e.g. the depth dose curve. Such adaptations may e.g. be included in the dose planning system.

Since the radiation head 8, in the embodiment of FIG. 11, performs a linear motion, the mechanical construction of means for performing a radiation head motion can be simpler and thereby cheaper than corresponding means for a circular motion, such as in FIG. 1. The less complicated construction is a substantial advantage, since the radiation head 8 typically involves large weights. With the linear configuration, the centre of mass will remain stationary in the radial direction, cancelling the need for dynamic balance means. Any reduced complexity in the motion of the radiation head 8 may thus lead to substantial construction advantages.

However, the reduced complexity in the radiation head translation also leads to an increased complexity in that the radiation head 8 has to be tilted in a controlled manner depending on the translation position. However, means for tilting the radiation head 8 can be made rather simple, since the weight of the radiation head 8 can be supported by separate means, e.g. by an axle, around which the radiation head 8 is tilted. The controlled tilting may e.g. be obtained by mechanical and/or electrical means according to conventionally available techniques.

Figure 12:
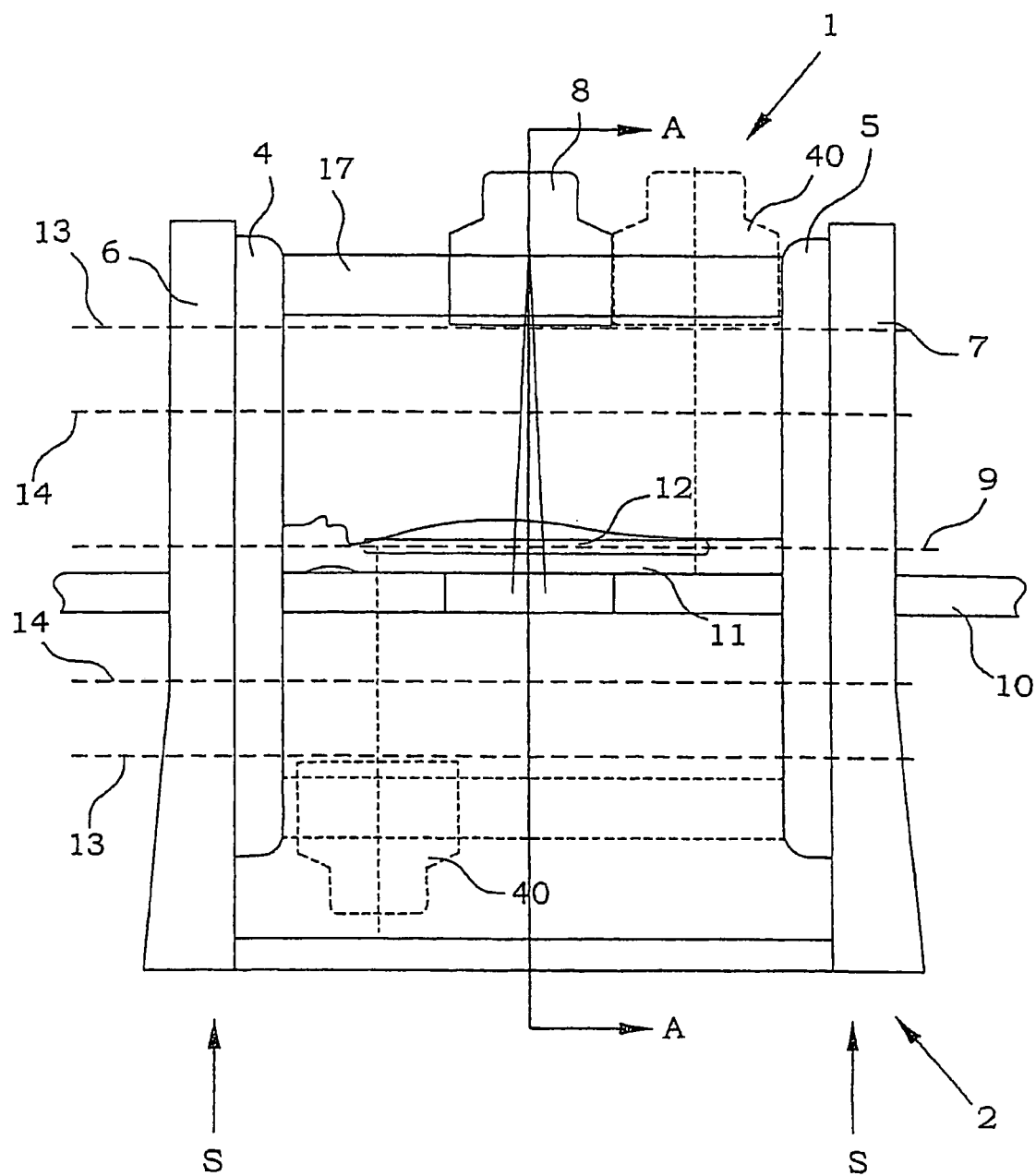
FIG. 12 is a side view of the embodiment of FIG. 11 used in a coplanar section mode.

FIG. 12 illustrates the embodiment of FIG. 11 in an alternative operational mode. In this case an extended treatment volume 12 is demanded. The radiation head 8 can in such cases be moved along the linear beam portion 17 without tilting and without any focusing adjustment, e.g. to the positions 40. A series of coplanar irradiation are thus achieved, or alternatively, if the translation is continuous, a treatment along a helical path. Other variants of controlling the tilting and focusing are, of course, also possible. The embodiment of FIGS. 11 and 12 may be advantageous for certain types of treatments, otherwise the embodiment of FIG. 1 is probably to prefer.

It will be understood by those skilled in the art that various modifications and changes may be made to the present invention without departure from the scope thereof, which is defined by the appended claims.

What is claimed is:

1. Irradiation device, comprising
    a gantry;
    said gantry comprising an inner gantry part and an outer gantry part;
    a radiation head, mechanically supported by said inner gantry part and rotatable around a rotation axis;
    said radiation head being arranged to direct radiation to a treatment volume situated substantially on said rotation axis;
    wherein all movable parts of said gantry are, in all situations, situated at a distance from said rotation axis larger than a predetermined value;
    said inner gantry part being rotatably supported by said outer gantry part at two support locations, situated on opposite sides of said treatment volume in a direction parallel to said axis;
    said outer gantry part being stationary with respect to said treatment volume;
    said radiation head being movable relative to said outer gantry along at least one arc of a circle substantially centered at said treatment volume;
    said arc being non-parallel with the rotation of said radiation head around said rotation axis, whereby non-coplanar irradiation treatment is achievable.

2. Irradiation device according to claim 1, wherein said gantry (1–2) is arranged substantially radially with respect to said treatment volume (12), as defined by said rotation axis (9).

3. Irradiation device according to claim 1, wherein said radiation head (8) is continuously rotatable around said rotation axis (9).

4. Irradiation device according to claim 1, wherein said inner gantry part (1) comprises a first ring portion (4) and a second ring portion (5) separated in the direction of the rotation axis (9), said ring portions (4, 5) being carried in a first support portion (6) and a second support portion (7) of said outer gantry part (2), respectively.

5. Irradiation device according to claim 4, wherein at least one of the pairs of said ring portions (4, 5) and said support portions (6, 7) comprises electrical connections with sliding contacts.

6. Irradiation device according to claim 4, wherein said inner gantry part (1) further comprises a circle arc portion (3), on which said radiation head (8) is movably supported, whereby the center of curvature of said arc portion (3) is situated in said treatment volume (12).

7. Irradiation device according to claim 1, further comprising means for numerical control of movable parts in said irradiation device.

8. Irradiation device according to claim 1, wherein said irradiation device further comprises a body-supporting couch (10), comprising two couch support portions (20, 21), situated on each side of said treatment volume (12), in the direction of said rotation axis (9).

9. Irradiation device according to claim 8, wherein said body-supporting couch (10) is formed in two rigid parts (22, 23), each one attached to a respective one of said couch support portions (20, 21), said rigid parts (22, 23) being interconnected by material (24) with a low radiation cross section.

10. Irradiation device according to claim 9, wherein said couch support portions (20, 21) are movable independently of each other.

11. Irradiation device according to claim 10, wherein said couch support portions (20, 21) are movable in two translational directions, substantially perpendicular to said rotation axis (9).

12. Irradiation device according to claim 8, wherein said body-supporting couch (10) is arranged within a distance of said predetermined value from said rotation axis (9).

13. Irradiation device according to claim 1, further comprising a body-supporting couch (10) that is elongated in the direction of said axis (9).

14. Irradiation device according to claim 13, wherein said body-supporting couch (10) is disposed below said axis (9).

15. Irradiation device according to claim 13, wherein said elongated body-supporting couch (10) has a lengthwise extent disposed parallel to said axis (9).

16. Irradiation device comprising:
    a gantry;
    said gantry comprising an inner gantry part and an outer gantry part;
    a radiation head, mechanically supported by said inner gantry part and rotatable around a rotation axis;
    said radiation head being arranged to direct radiation to a treatment volume situated substantially on said rotation axis;
    wherein all movable parts of said gantry are, in all situations, situated at a distance from said rotation axis larger than a predetermined value;
    said inner gantry part being rotatably supported by said outer gantry part at two support locations, situated on opposite sides of said treatment volume in a direction parallel to said axis;
    said inner gantry part further comprising a linear beam portion, on which said radiation head is movably supported for motions along said linear beam portion;
    said linear beam portion mechanically connecting said two support locations; and
    said linear beam portion being substantially parallel to said rotation axis;
    wherein said radiation head is tiltably supported by said linear beam portion, said radiation head directing its radiation towards said treatment volume from any position relative to said linear beam portion.

* * * * *